United States Patent [19]

Etscorn

[11] Patent Number: 4,597,961
[45] Date of Patent: Jul. 1, 1986

[54] TRANSCUTANEOUS APPLICATION OF NICOTINE

[76] Inventor: Frank T. Etscorn, 121 Stallion Cir., Socorro, N. Mex. 87801

[21] Appl. No.: 694,047

[22] Filed: Jan. 23, 1985

[51] Int. Cl.[4] .................... A61K 9/70; A61K 31/465
[52] U.S. Cl. .................................... 424/28; 514/314; 514/813
[58] Field of Search .................... 424/14, 28; 514/343, 514/813

[56] References Cited

U.S. PATENT DOCUMENTS

| 1,775,998 | 9/1930 | Greenberg | 604/304 |
| 3,598,122 | 8/1971 | Zaffaroni | 604/304 |
| 3,598,123 | 8/1971 | Zaffaroni | 604/304 |
| 3,731,683 | 5/1973 | Zaffaroni | 424/28 |
| 3,742,951 | 7/1973 | Zaffaroni | 424/28 |
| 3,948,254 | 4/1976 | Zaffaroni | 604/57 |
| 4,292,299 | 9/1981 | Suzuki et al. | 424/28 |

OTHER PUBLICATIONS

The Merck Index-Tenth Edition, 1983, Published by Merck & Co., Inc. Rahway, N.J., U.S.A., p. 935.
Drug Alcohol Dependence, 13 (1984), pp. 209–213 Elsevier Scientific Publishers Ireland Ltd.

*Primary Examiner*—Ronald W. Griffin
*Attorney, Agent, or Firm*—Browdy & Neimark

[57] ABSTRACT

Percutaneous administration of nicotine in a dose approximating the dose delivered by a variety of nicotine-containing products, such as cigarettes, cigars, snuff and chewing tobacco, is carried out using an occlusive pad. The nicotine is delivered so as to mimic the pharmacological effects of nicotine provided by the conventional use of tobacco, and a therapeutic function is achieved by reducing or eliminating the need for the tobacco product. A suitable transdermal application pad comprises a reservoir for liquid nicotine base to be affixed to the skin in a variety of places. Due to the high lipid solubility and resultant high skin permeability of nicotine, vehicles or solvents are not generally needed to enhance dermal absorption.

19 Claims, 2 Drawing Figures

TRANSCUTANEOUS APPLICATION OF NICOTINE

FIELD OF THE INVENTION

The present invention relates to the cutaneous administration of nicotine, and more especially to a new method of administering nicotine through the skin using a transdermal delivery system, especially for the purpose of satisfying a nicotine habit while minimizing or eliminating side effects caused by absorbing tobacco constituents through the lungs along with products of combustion of tobacco.

BACKGROUND OF THE INVENTION

The health hazards from tobacco smoking are well established. Of the approximately 4,000 by-products of combustion found in cigarette smoke, many of which are known carcinogens, the three substances studied most have been tars, carbon monoxide and nicotine. Tars and carbon monoxide hae been directly implicated in the production or exacerbation of numerous health disorders.

Thus, tars are the causitive agents in cigarette smoke most implicated in the induction of such cancers as lung, larynx, oral cavity, esophageal, bladder, kidney, pancreatic stomach, and uterine and cervix cancers. Tars are also considered responsible for the induction of the hepatic microsomal ensyme systems which result in more rapid deactivation of a variety of drugs such as benzodiazepines as well as anti-depressants and analgesics. Tars are also responsible for the production of bronco pulmonary diseases, including pulmonary emphysema, chronic bronchitis and smokers respiratory syndrome.

Carbon monoxide, a deadly gas, is an important health hazard even in minute quantities because it combines with the hemoglobin in the blood so that the hemoglobin can no longer carry sufficient oxygen. Moreover, the stimulant effect of the nicotine in the smoke causes an increase in cardiac workload and oxygen demand, whereas the carbon monoxide effectly blocks the ability of the heart muscle to capture the needed oxygen. In other words, carbon monoxide and nicotine work together in a synergistically negative manner in a way which often results in anoxia and ultimately in cardiac damage. In addition, carbon monoxide has also been implicated as a causative agent in the development of such disorders as coronary artery disease and atherosclerosis.

Nicotine appears to be the most pharmacologically active substance in tobacco smoke, yet it appears to be not as significant from a health standpoint as the tars and carbon monoxide. However, nicotine is very important from another standpoint, i.e. it is the reinforcing substance in tobacco which maintains the addiction. In this respect, a theme commonly heard among workers in the field of smoking research is, "People would be disinclined to smoke cigarettes if an alternate route of nicotine delivery could be devised."

Several such attempts have been made to administer nicotine in alternate ways, but with varying and generally ineffective results. For example, nicotine-containing pills have been studied; however, effective blood levels of nicotine are not achieved because drugs absorbed in the stomach pass through the liver first where, in this case, 80–90 percent of nicotine deactivation occurs. Similar findings have been demonstrated with nicotine chewing gum although it has been sufficiently successful to warrant its marketing.

There are other long established and traditional ways of absorbing nicotine through the mouth, including chewing tobacco, snuff and the newly introduced products such as "Bandits" which constitute diffusion bags of tobacco, all of such means relying on oral (or nasal) absorption of nicotine through the mucous membrane. However, because of the taste and other sensory effects of tobacco, such a manner of satisfying the nicotine habit is acceptable to only a very limited number of persons. Moreover, these habits still require the utilization of tobacco, and such use remains a problem especially for people with gum, mouth or throat problems as a result of long-term tobacco chewing or snuff "dipping" and who are unable to quit.

With regard to the nicotine gum referred to above, it has produced mouth ulcers in a number of individuals resulting in its rejection. In addition, the nicotine gum produces some gastric absorption with the resultant first pass through the liver and consequent rapid loss of activity. Moreover, first hand reports indicate that some people using the gum rejected it on the basis of taste. Moreover, denture wearers have difficulty with gum in general; this is important as many people who experience the medical problems associated with years of smoking may also be denture wearers.

Nicotine itself has been subjected to considerable study. Nicotine is a liquid alkaloid which is colorless, volatile and strongly alkaline. On exposure to air it turns brown. It is known to be very lipid soluble. The Merck Index, 9th Edition, 1976, page 847, indicates that nicotine base is readily absorbed through mucous membrane and intact skin, but the salts are not. On the other hand, nicotine has no known therapeutic application (The Pharmacological Basis of Therapeutics, fifth edition, Goodman and Gilman, 1970, page 467) and has been primarily used in research as an experimental tool for investigating neural function.

It is known to administer a wide variety of pharmaceuticals transdermally through the skin, and two patents which disclose bandages for administering drugs are the Zaffaroni U.S. Pat. Nos. 3,598,122 and 3,948,254. Drugs indicated to be administerable include anti-microbials sedatives, hypnotics, psychic energizers, tranquilizers, hormones, anti-pyrectics, anti-diabetics, cardovascular agents, anti-spasmatics, anti-malarials, decongestants, nutritional agents, anti-bacterials, anti-neoplastics, anti-inflammatory agents, desensitizing agents, vaccines, anti-allergics, anti-fungals, anti-perspirants, deodorants, astringents and irritants. Thus, while the field of drugs and pharmaceuticals mentioned in these patents is very wide, there is no disclosure of administration of nicotine; and nicotine appears to have few properties in common with the categories of drugs mentioned in these patents. In view of the fact that nicotine has no therapeutic use, its relationship to any agents mentioned in these patents appears even more remote.

It is further known that the absorption of many topically applied drugs may be enhanced by occlusion, which consists of covering the treated skin with an impermable plastic sheet or film which prevents water evaporation or drug decomposition. Under such circumstances the keratin layer then becomes softer and less effective as a bearer, so that absorption of the drug is facilitated (Annual Review of Medicine, Volume 33, Chapter 18, 1982, "The Principles of Drug Therapy in Skin Disorders", R.C. Heading, pages 475,476).

Insofar as is known, it has not previously been proposed to transdermally administer a drug for the purpose of reducing or eliminating a dependence, or for administering a drug of addiction in a manner that is safer and less damaging than the route by which such drug is normally administered. Insofar as is known, no ganglionic stimulating agent has been previously delivered transdermally, and it is believed that it has not been previously proposed to administer nicotine transdermally.

SUMMARY OF INVENTION

It is, accordingly, an object of the invention to overcome problems in the prior art, such as indicated above.

It is another object to administer nicotine through the skin using a transdermal delivery system, especially for the purpose of satisfying a nicotine habit while minimizing or eliminating side effects caused by absorbing nicotine through the lungs along with products of combustion of tobacco.

It is a further object of the invention to provide a new method of assisting persons break the habit of smoking tobacco or the use of any tobacco product.

It is still another object of the invention to provide a nicotine transdermal delivery system.

These and other objects of the invention are broadly achieved by providing nicotine in a form, such as on a bandage or the like, whereby it is applied to the skin and permitted to enter the body transdermally. Under such conditions the nicotine, being highly lipid soluble, is absorbed directly and rapidly through the skin thereby satisfying the nicotine habit while minimizing or eliminating side effects which would otherwise be caused when absorbing nicotine through the lungs along with products of combustion. Such a delivery system can also assist a person to quit smoking.

A transdermal bandage containing a reservoir of nicotine may be applied to a variety of inconspicuous places on the human body, e.g. the postauricular area. By supplying the smoker with an alternate source of nicotine in the dose range of from 15 to 25 nanograms per liter of blood, the need for cigarettes is reduced or eliminated. Using such a mode of administration provides a number of beneficial results as follows:

1. An improved system becomes available to aid motivated smokers in eliminating their cigarette addiction. Numerous potent non-pharmacological factors which help maintain the cigarette addiction are the rituals involved with the act of smoking, including the sight of a pack of cigarettes, the smell, the taste, etc. These previously neutral cues acquire powerful reinforcing properties as a result of prolonged associations with nicotine. Practice of the present system, however, assists in extinguishing these addiction-maintaining cues by supplying nicotine in the absence of such cues.

Indeed, a plurality of extinguishing techniques can be utilized in association with the present invention. Thus, instead of completely substituting the technique of the instant invention for smoking, an interspercing regimen can be adopted wherein nicotine-containing transderms according to the invention may be alternated with cigarettes to slowly extinguish the reinforcing properties of the non-pharmacological factors, and also reduce the severity of the initial termination of smoking as well as the incidence of relapse. As the non-pharmacological factors become reduced in importance, it then upon becomes easier to treat the nicotine addiction.

2. Patients with disorders such as emphysema, cardiac problems or lung cancer and who are unable to quit smoking thus exasperating their medical problems are able to satisfy their nicotine habit while sparing themselves further damage from the tars and carbon monoxide in tobacco smoke.

3. Nicotine absorbed transdermally is not transported first pass through the liver where 80–90 percent of nicotine deactivation occurs, but goes directly and rapidly into systemic circulation with rapid rises in nicotine blood level. Thus, the nicotine habit can be satisfied while subjecting the body to far lesser quantitites of nicotine.

4. Using the present system, blood levels of nicotine can be easily adjusted to acceptable and effective dosages for the suppression of craving by varying the amount and duration of nicotine delivery. This is difficult if not impossible to accomplish with nicotine gum, because the person's rate of chewing is a major factor which manipulates dosage.

5. People with gum, mouth and throat problems, as a result of long-term tobacco chewing or snuff "dipping" and who are unable to quit, are aided in giving up their habits with the use of transdermally applied nicotine.

6. Other advantages compared to nicotine containing gum include obviating the problems of mouth ulcers in some individuals; elimination of nicotine taste as a secondary reinforcer; provision of a less conspicuous form of nicotine consumption (a cutaneous patch is much less conspicuous than gum chewing; for example, in stressful situations which typically serve as cues for smoking, such as business meetings, etc., gum chewing is less acceptable than the use of a transdermal patch); usability by those who reject gum on the basis of taste and some denture wearers who cannot chew gum; and provision of an alternate mode of nicotine administration. In this latter respect, even if the transdermal administration is only equal in effectiveness to nicotine gum for many persons, this will provide a further method of reducing smoking dependence, it being known in the field that different techniques work better for different individuals.

7. In the event that the subject of the instant invention becomes available over-the-counter (as are cigarettes, snuff, chewing tobacco, etc.), the instant invention will provide a means for those, unable or unwilling to quit smoking, to ingest nicotine without subjecting themselves and their environment to smoking with its attendant dangers of carbon monoxide and tars. It would also allow ingestion of nicotine in places where smoking is prohibited, to avoid the consequences of performance decrements resulting from acute withdrawals. Moreover, for women unable to quit smoking during pregnancy, transdermal nicotine would at least eliminate carbon monoxide, thereby avoiding the deliterious effects of smoking on the fetus due to the blocking effects of carbon monoxide on oxygen absorption.

BRIEF DESCRIPTION OF DRAWING

For a better understanding of the invention, as well as the above and other objects and the nature and advantages of the instant invention, possible embodiments thereof will now be described with reference to the attached drawings, it being understood that these embodiments are intended as merely exemplary and in no way limitative.

DETAILED DESCRIPTION OF EMBODIMENTS

Figure 1:
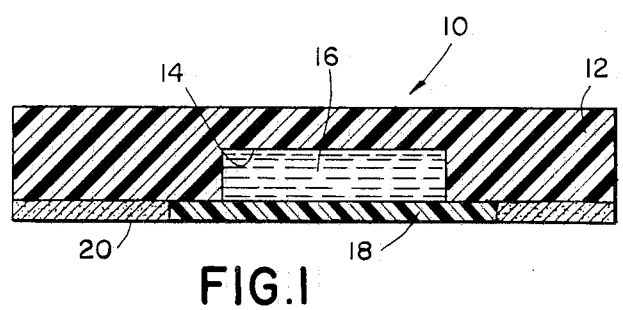
FIG. 1 is a schematic cross-sectional view of a first embodiment of the invention.

FIG. 1 is a schematic cross-sectional view of a nicotine-containing transdermal bandage 10 having a width or diameter of about 1.5 centimeters and a thickness of about 2.0 centimeters. It comprises a nicotine impermeable backing 12 formed of a suitable, preferably flexible and impervious plastic or rubber material, such as polyvinylidene chloride, polyethylene, polypropylene, nylon, silicone rubber, etc., having a cavity 14 along one surface thereof. Within the cavity 14 is provided liquid nicotine 16 in an amount of 1–4 microliters. Sealing the nicotine film 18, again formed of a suitable microporous and flexible plastic or rubber which is inert to the nicotine. Lastly, suitable adhesive 20 is provided on either side of, or completely around the nicotine permeable membrane.

The precise nature of the materials from which the bandage 10 are formed may be easily determined from common knowledge, such as disclosed in the aforementioned Zaffaroni patents, coupled if necessary with routine testing for inertness relative to nicotine. The bandage 10 may be kept sealed in an air-tight pouch prior to use to prevent reaction of the nicotine with air.

Figure 2:
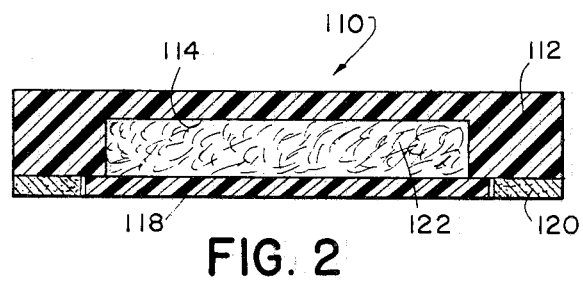
FIG. 2 is a schematic cross-section view of a second embodiment according to the present invention.

FIG. 2 shows a second embodiment of a nicotine bandage 110 having a nicotine impermeable backing 112 with a relatively large cavity 114, and which may or may not be covered with a nicotine permeable membrane or microporous film 118. The reservoir 114 is surrounded with adhesive 120. Located within the cavity is a suitable absorbant material 122, such as a sponge or cotton, on which is absorbed the desired quantity of liquid nicotine, preferably in the range of 1–4 microliters to provide a dosage desirably in the range of about 15–25 nanograms per liter of blood per administration.

Dosage and duration of nicotine administration transdermally according to the present invention can be controlled in several ways separately and in combination. In general, a carrier can be mixed with the nicotine which will either speed or slow its passage through the microporous membrane and/or into the skin. The thickness, number of pores and/or size of pores can be varied to either increase or decrease the speed of passage of nicotine through the microporous membrane. The quantity of nicotine in the reservoir can be either decreased or increased to reduce or increase the duration or amount of dosing. All other factors being equal, use of the embodiment 10 of FIG. 1 will give a smaller dose over a longer term compared with use of the embodiment 110 of FIG. 2, merely because of the presence of the microporous membrane 18 which slows the delivery of the nicotine to the skin.

In general, no additive is necessary to assist in the transdermal administration of nicotine, because nicotine base is very highly lipid soluble and is quickly and completely absorbed into the systemic circulation. However, should it be desirable to increase or decrease the rate of penetration, then the nicotine base can be carried by a suitable solvent such as propylene glycol, glycerin, mineral oil, polyethylene glycol, DMSO or alcohol. It may also be mixed with water in which the alkaloid is readily soluble, thereby forming a water soluble salt; such a salt, however, is less lipid soluble and penetrates the skin much more slowly than the alkaloid base.

It may be desirable to add a carrier which will slow absorption in view of the fact that nicotine is highly toxic. In this way, the nicotine may be diluted to reduce dangers of misuse; for example, the nicotine may be mixed with an oil such as indicated above, or preferably an oil having an unpleasant taste, such as castor oil. Other types of fillers may be utilized as well; for example, the nicotine may be retained in a gelatinous base. Other additives may be incorporated to reduce the possibility of accidental oral ingestion, such as a mercaptan.

Using transdermal delivery while varying the porosity of the membrane separating the nicotine from the person's skin and/or the quantity of nicotine and manner in which it is retained, the dose and duration of nicotine administration are precisely controllable. Also, the total dosage and delivery rate can easily be adjusted to suit the needs of the particular patient, i.e. a different dose of nicotine will be desirable to reduce the craving of a one pack-a-day smoker versus a three pack-a-day smoker. According to the present invention, it is possible to mimic smoking in terms of the amount of nicotine delivered, thereby reducing or eliminating dependence on any form of tobacco.

It is preferred that the nicotine be administered transdermally using an occlusive technique, i.e. the use of a pad in which the backings (e.g. backing 12 or 112 in the illustrated embodiments) are impermeable and opaque to provide protection from light and air so as to insure transport across the skin before the nicotine has a chance to become deactivated. Aternatively, a less impervious backing 12 or 112 can be used, and the entire pad can be covered with an impervious plastic covering.

It is preferred that the pad 10 or 110 or the like be placed inconspicuously on an area of the skin such as behind the ear. This postauricular area insures rapid transport to the brain with little blood dilution. Alternatively, the pad can be placed elsewhere such as on the underside of the wrist, in which case there is delayed transport of the nicotine to the brain with enhanced blood dilution. The particular areas selected is determined on the basis of the severity of the addiction. The onset of nicotine activity is in the range of 1–2 minutes with a duration of action up from 30–45 minutes, these values varying as a function of the dose administered, the permeability of the porous membrane, the surface area covered by the nicotine, and the site of application.

The following examples will further illustrate ways in which the present invention can be practiced, it being understood that the specific conditions set forth are not to be considered limiting of the invention.

COMPARATIVE EXAMPLE ONE

A series of tests were conducted on rats for the purpose of flavor aversion learning. Thus, if a rat is made to sample a novel flavor such as saccharin and several hours later subjected to gastrointestinal malaise from X-irritation, drug injection or rotational stimulation, the rat will reject the once-palatable flavor if it is subsequently offered. In essense, the rat behaves as though the saccharin were responsible for the illness. In this test, it was attempted to provide the gastro-intestinal malaise by administration of 2 mg/kg of IP nicotine base. A thirty-minute delay was interposed between the end of drinking the saccharin (15 minutes were allowed for drinking) and the nicotine injection. Four groups of rats were used, one being injected with physiological saline, one with 0.5 mg/kg of nicotine base, the third with 1.0 mg/kg of nicotine base and the fourth with 3.0 mg/kg of nicotine base, all IP.

No evidence of aversion was found in these animals. It appeared that the half-life of nicotine was two short for a version acquisition. In addition, the rats administered 3 mg/kg all convulsed possibly conducing a retrograde amnesic effect.

EXAMPLE 1

Eight studies were conducted analogous to comparative example 1 above, except that the nicotine was administered transcutaneously to the rats.

One of these studies involved giving unshaved rats either saline, or 10, 30 or 50 mg/kg of nicotine 30 minutes after having sampled the saccharin solution. The nicotine was applied to an area approximately one inch behind each animal's head in order to eliminate the possibility of the animal ingesting the drug while grooming. There was a reliable dose-response effect and strong aversions developed to the saccharin solution. The more nicotine applied, the greater the unwillingness of the rats to drink saccharin solution. In addition, the duration of the illness was considerably longer than with the IP injected nicotine of comparative example 1. This study demonstrated that it was possible to absorb sufficient nicotine through the skin to produce enough nausea for conditioning flavor aversion.

Other studies in this series involved various techniques for removing hair at the site of transdermal application of the nicotine. In one study the depillatory, "Nair", was used. However, it adversely affected skin permeability for several days after its use and rendered previously tolerable dosages of nicotine quite toxic producing profound convulsions.

In a later study in the series, the fur of the rats was shaved in the area of transdermal application. This permitted application of much smaller dosages and suggested that application of nicotine to the unshaved skin produced a "wicking" by the fur of a sizable portion of the nicotine away from the skin, with result that the nicotine became decomposed to some extent. Doses of 3, 9 and 27 mg/kg in shaved rats produced virtually identical aversions as 10, 30 and 50 mg/kg, respectively, in unshaved rats.

In a further study, mixing of the nicotine with DMSO in ratios of 1:1 and 1:4 of nicotine: DMSO for the purpose of producing more rapid absorption, caused a raised blister on the skin of shaved rats.

EXAMPLE 2

In order to test transcutaneous application, the present inventor applied to himself, in the postauricular area on several occasions, 3 mg and 5 mg respectively of nicotine base. Nausea was not induced at these dose levels although some effect was felt at the 5 mg level.

EXAMPLE 3

A bandage is made as shown in FIG. 1 consisting of an occulsive pad 10 including a backing 12 approximately 1.5 cm in diameter containing a reservoir 14 filed with nicotine base. The reservoir contains from 1 to 4 microliters of nicotine, roughly equivalent to 1–4 mg. To use the pad, a protective nicotine impermeable sealant film consisting of plastic or waxed coated paper, alumimun foil or a variety of other sealant materials is provided to cover the nicotine reservoir. This sealant film is stripped from the pad immediately prior to usage.

A microporous nicotine permeable membrane 18, having a thickness of 20–50 microns, covers the reservoir 14. On application of the pad 10, the membrane 18 contacts the skin. The nicotine impermeable backing layer 12 essentially encloses or covers the nicotine 16 and forms the actual reservoir 14 to protect the drug from breakdown as a result of exposure to light or air, and permits prolonged storage.

The backing layer may be formed from such materials as silicone rubber or plastic. The nicotine permeable membrane as well as the high lipid solubility of nicotine insures rapid transport the via passive diffusion from the reservoir 14 through the skin to the underlying vascularized tissue. Around the outer margin of the pad is a layer of pressure-sensitive or contact adhesive 20 designed to attach the pad firmly to the skin as well as to provide a tight seal to prevent the drug from leaking from under the pad.

EXAMPLE 4

A bandage is made as shown in FIG. 2 comprising an occlusive pad 110 with a backing 112 approximately 1.5 cm in diameter and having an open reservoir 114 covered by a nicotine impermeable sealant film to be removed before application of the pad 110 to the skin. The open reservoir 114 contains a dense matrix of inert fibrous or porous material, such as cotton, to prevent spillage of the nicotine prior to application of the pad to the skin. In use, the nicotine wicks from the cotton matrix as the nicotine diffuses across the skin.

The foregoing description of the specific embodiments will so fully reveal the general nature of the invention that others can, by applying current knowledge, readily modify and/or adapt such specific embodiments without departing from the generic concept, and, therefore, such adaptations and modifications should and are intended to be comprehended within the meaning and range of equivalents of the disclosed embodiments. It is to be understood that the phrasiology or terminology employed herein is for purposes of description and not of limitation.

What is claimed is:

1. A method of administering nicotine for the purpose of satisfying a nicotine habit while minimizing or eliminating side effects caused by absorbing nicotine through the lungs along with products of combustion of tobacco, comprising transdermally administering nicotine via an occlusive pad adhered to the skin at a dosage rate sufficient to satisfy said nicotine habit, said occlusive pad comprising a nicotine-impermeable backing and nicotine-permeable, porous, inert membrane, said nicotine impermeable backing and said nicotine-permeable membrane defining a cavity therebetween, said cavity containing liquid nicotine therein.

2. A method according to claim 1 wherein said nicotine is in the form of nicotine base without a solvent, vehicle or carrier.

3. A method according to claim 1 wherein said nicotine is in the form of nicotine base diluted with a pharmaceutically acceptable carrier, solvent or vehicle which reduces penetration of the nicotine base through the skin.

4. A method according to claim 1 wherein said nicotine is administered by application to the skin behind the ear.

5. A method according to claim 1 wherein said pad comprises 1–4 microliters of nicotine base.

6. A method according to claim 1 wherein said nicotine is transdermally administered at a dosage rate of 15-25 nanograms per liter of blood.

7. A method of administering nicotine for the purpose of satisfying a nicotine habit in accordance with claim 1, wherein said nicotine is transdermally administered to a patient physically addicted to nicotine.

8. A method of assisting a person to quit smoking, comprising transdermally administering nicotine via an occlusive pad adhered to the skin at at a dosage rate approximately the same as provided when absorbing nicotine by smoking, said occlusive pad comprising a nicotine-impermeable backing and nicotine-permeable, porous, inert membrane, said nicotine-impermeable backing and said nicotine-permeable membrane defining a cavity therebetween, said cavity containing liquid nicotine therein.

9. A method according to claim 8 comprising carrying out a series of said transdermal administrations and interspercing said transdermal administrations with cigarettes to slowly extinguish the reinforcing properties of non-pharmacological factors.

10. A method according to claim 8 wherein said pad comprises 1-4 microliters of nicotine base.

11. A method according to claim 10 wherein said nicotine is in the form of nicotine base without a solvent, vehicle or carrier.

12. A method according to claim 10 wherein said nicotine is in the form of nicotine base diluted with a pharmaceutically acceptable carrier, solvent or vehicle which reduces penetration of the nicotine base through the skin.

13. A method according to claim 10 wherein said nicotine is administered by application to the skin behind the ear.

14. A method according to claim 8 wherein said nicotine is transdermally administered at a dosage level of 15-25 nanograms per liter of blood.

15. A method of administering nicotine for the purpose of satisfying a nicotine habit in accordance with claim 8, wherein said nicotine is transdermally administered to a patient physically addicted to nicotine.

16. A method of administering nicotine for the purpose of satisfying a nicotine habit while minimizing or eliminating side effects caused by absorbing nicotine through the lungs along with products of combustion of tobacco, comprising transdermally administering nicotine via an occlusive pad adhered to the skin at a dosage rate sufficient to satisfy said nicotine habit, said occlusive pad comprising a nicotine impermeable backing defining a cavity therein, and an absorbant material having absorbed nicotine therein, within said cavity.

17. A method according to claim 16 wherein said pad comprises 1-4 microliters of nicotine base.

18. A method of assisting a person to quit smoking, comprising transdermally administering nicotine via an occlusive pad adhered to the skin at a dosage rate approximately the same as provided when absorbing nicotine by smoking, said occlusive pad comprising a nicotine impermeable backing defining a cavity therein, and an absorbant material having absorbed nicotine therein within said cavity.

19. A method according to claim 18 wherein said pad comprises 1-4 microliters of nicotine base.

* * * * *

UNITED STATES PATENT AND TRADEMARK OFFICE
CERTIFICATE OF CORRECTION

PATENT NO.   : 4,597,961

DATED        : July 1, 1986

INVENTOR(S)  : Frank T. Etscorn

It is certified that error appears in the above-identified patent and that said Letters Patent is hereby corrected as shown below:

Column 3, line 45: replace "liter" with --milliliter--.
Column 5, line 39: replace "liter" with --milliliter--.
Column 9, line 3, claim 6, replace "liter" with --milliliter--.
Column 10, line 6, claim 14, replace "liter" with --milliliter--.

Signed and Sealed this

Eighth Day of December, 1992

Attest:

DOUGLAS B. COMER

Attesting Officer

Acting Commissioner of Patents and Trademarks